US008153685B2

(12) United States Patent
Gastner et al.

(10) Patent No.: US 8,153,685 B2
(45) Date of Patent: Apr. 10, 2012

(54) SALTS, ADDITION COMPOUNDS AND COMPLEX COMPOUNDS OF GUINADINOACETIC ACID

(75) Inventors: Thomas Gastner, Engelsberg (DE); Hans-Peter Krimmer, Kirchweidach (DE)

(73) Assignee: Alzchem Trostberg GmbH, Trostberg (DE)

( * ) Notice: Subject to any disclaimer, the term of this patent is extended or adjusted under 35 U.S.C. 154(b) by 299 days.

(21) Appl. No.: 11/885,375

(22) PCT Filed: Mar. 2, 2006

(86) PCT No.: PCT/EP2006/001908

§ 371 (c)(1), (2), (4) Date: Aug. 30, 2007

(87) PCT Pub. No.: WO2006/092298

PCT Pub. Date: Sep. 8, 2006

(65) Prior Publication Data

US 2008/0161387 A1 Jul. 3, 2008

(30) Foreign Application Priority Data

Mar. 4, 2005 (DE) ........................ 10 2005 009 990

(51) Int. Cl.
*A01N 43/30* (2006.01)
*A01N 43/26* (2006.01)
*A01N 43/16* (2006.01)

(52) U.S. Cl. ......... 514/464; 514/440; 514/554; 514/460

(58) Field of Classification Search .................. 514/464, 514/440, 460, 554

See application file for complete search history.

(56) References Cited

U.S. PATENT DOCUMENTS 5,939,078 A 8/1999 Fujimura et al.
6,242,491 B1 6/2001 Kaddurah-Daouk
6,855,727 B2 * 2/2005 Matahira et al. ............. 514/396
7,186,754 B2 * 3/2007 Kaddurah-Daouk ......... 514/565
2002/0049253 A1 4/2002 Kaddurah-Daouk
2005/0287204 A1 12/2005 Hageman et al.

FOREIGN PATENT DOCUMENTS

GB 1 195 199 A 6/1970
GB 1 195 200 A 6/1970
JP 61-231996 A 10/1986
WO WO-91/07954 A 6/1991
WO WO-01/00203 A 1/2001
WO WO-04/000297 A 12/2003
WO WO-2005/120246 A 12/2005

OTHER PUBLICATIONS

Thoai et al. STN Accession No. 1965:4409DOCUMENT No. 62:4409, Abstract of Comptes Rendus des Seances de la Societe de Biologie et de Ses Filiales (1953), 147, 1241-3.*

STN Document No. 144:50700 shows structure RN for phosphate salt of guanidinoacetic acid.*

STN Document No. 62:4409 shows structure RN for phosphate salt of guanidinoacetic acid.*

De Miranda L., et al. "Study on guinidino-carboxylate interactions with copper (II) ternary complexes of guinidinoacetic acid with glutamic and aspartic acid", Polyhedron, (2003).

* cited by examiner

*Primary Examiner* — Nizal Chandrakumar

(74) *Attorney, Agent, or Firm* — Fulbright & Jaworski L.L.P.

(57) ABSTRACT

The present invention provides new salts and/or addition compounds and/or complex compounds of guanidinoacetic acid with malic acid, aspartic acid, ascorbic acid, succinic acid, pyruvic acid, fumaric acid, gluconic acid, α-ketoglutaric acid, oxalic acid, pyroglutamic acid, 3-nicotinic acid, lactic acid, citric acid, maleic acid, sulfuric acid, acetic acid, formic acid, 2-hydroxybenzoic acid, L-carnitine, acetyl-L-carnitine, taurine, betaine, choline, methionine and lipoic acid as well as in the form of sodium, potassium or calcium guanidinoacetate. These salts have improved physiological and therapeutic properties and are particularly suitable for use as dietary supplements, as animal feeds and in cosmetic or dermatological preparations in which especially the marked stability and good bioavailability of the salts come to the fore.

30 Claims, No Drawings

SALTS, ADDITION COMPOUNDS AND COMPLEX COMPOUNDS OF GUINADINOACETIC ACID

This is a §371 of PCT/EP2006/001908 filed Mar. 2, 2006, which claims priority from German Patent Application Nos. 10 2005 009 990.4 filed Mar. 4, 2005.

The present invention concerns the preparation of new salts, addition compounds and complex compounds of guanidinoacetic acid. They have improved physiological and therapeutic properties and are suitable for use as food supplements, animal feeds and in cosmetic or dermatological preparations in which especially their marked stability and good bioavailability of the salts come to the fore.

Guanidinoacetic acid is an endogenous substance which occurs in humans and plays a central role in the biosynthesis of creatine. Creatine is of major importance for the energy metabolism of the cell and it is taken up from the food and can also be formed by the body. The biosynthesis starts from glycine and L-arginine. In mammals the guanidino group of L-arginine is cleaved and an N—C—N group is transferred to glycine by the enzyme aminotransferase above all in the kidneys, but also in the liver and pancreas. In this process L-arginine is converted into L-ornithine. The guanidinoacetic acid formed in this manner is converted into creatine in the next step with the aid of the enzyme transmethylase and this occurs exclusively in the liver in the case of vertebrates.

Creatine in the form of energy-rich phosphocreatine is an important energy reserve of muscle in addition to adenosine triphosphate (ATP). When the muscle is in a resting state, ATP can transfer a phosphate group to creatine to form phosphocreatine which is then in direct equilibrium with ATP. During muscular work it is of decisive importance to fill up the ATP stores again as rapidly as possible. Phosphocreatine is available for this purpose in the first seconds of maximum muscular load. The enzyme creatine kinase can transfer a phosphate group from phosphocreatine to adenosine diphosphate in a very rapid reaction and thus re-form ATP. This is also referred to as the Lohmann reaction.

In the nineties creatine monohydrate became a popular dietary supplement due to its unique function in energy metabolism. The sports industry uses creatine monohydrate to increase the pool of energy-rich phosphate compounds in the body during training and to improve the body-mass index. Recent studies with creatine yielded positive therapeutic results for diverse clinical applications [Persky, A. M.; Brazeau, G. A.: Clinical Pharmacology of the Dietary Supplement Creatine Monohydrate. In: Pharmacol. Rev. 2001, 53, 161-176]. In addition to creatine itself i.e. creatine monohydrate, numerous creatine salts such as creatine ascorbate, creatine citrate, creatine pyruvate and others have also in the meantime proven to be suitable dietary supplements or therapeutic agents. The European Patent EP 894 083 and the German laid-open Patent Application DE 197 07 694 A1 are mentioned here as representatives.

In a series of scientific papers it was shown that creatine and its salts lead to an increase in fat-free muscle mass and muscle performance. Thus it is also known that the pancreas secretes more insulin under the influence of guadine compounds such as creatine and guanidinoacetic acid, and guanidinoacetic acid is substantially better at stimulating the secretion of insulin than creatine itself. Insulin promotes the uptake of glucose and amino acids into muscle cells and thus promotes protein synthesis. It is also advantageous that insulin catalyses the uptake of creatine into muscles. In addition insulin reduces the rate of degradation of the musculature.

Positive effects have also been found in animals and creatine monohydrate was therefore recommended for use as a feed additive and has a meat meal substitute in animal nutrition. Since the prohibition of animal proteins in feedstuffs in the year 2000 in the EU, many diets for breeding animals and fattened animals have been converted to pure vegetarian diets, and fish meal which was not covered by the ban has also been omitted to a large extent. The conversion to pure vegetarian diets led to losses in performance and, even after almost five years, the pure vegetarian diets are inferior to those containing animal proteins. One reason for this inferiority is the lack of creatine. Earlier experiments clearly showed that creatine monohydrate added to the feed can improve the performance when pure vegetarian diets are fed [Wallimann, T.; Pfirter, H. P.: Use of Creatine as a Feed Additive. EP1051914].

In addition to the undoubted positive effects creatine monohydrate also has some disadvantages. This compound has a very limited stability in aqueous solutions and creatine monohydrate only has a low bioavailability after oral ingestion. Furthermore, creatine monohydrate is a very expensive substance and the improvements in performance that were achieved in animal fattening are almost completely compensated by the costs.

Hence, guanidinoacetic acid which has an astounding stability in aqueous solution compared to creatine and is much more bioavailable, has also been used recently as a dietary supplement and animal feed. Guanidinoacetic acid is very efficiently and rapidly converted into creatine in the body. Hence, guanidinoacetic acid can be administered in substantially lower amounts than creatine while having the same effect. In one study, rats were fed diets containing about 0.36 g/kg guanidinoacetic acid by which means the creatine content in muscles increased by 39% compared to the comparison group [Stead, L. M.; Au, K. P.; Jacobs, R. L.; Brosnan, M. E.; Brosnan, J. T.: Methylation demand and homocysteine metabolism: Effects of Dietary Provision of Creatine and Guanidinoacetate. In: Am. J. Physiol. Endocrinol. Metab., 2001 November; 281(5); 1095-100]. The increase in creatine in muscle is due to a high conversion rate of the ingested guanidinoacetic acid into creatine. This also coincides with the observation that the enzyme transmethylase is found in very high concentrations in the liver.

In addition to its use as a dietary supplement or as an animal feed additive, guanidinoacetic acid is also suitable for cosmetic applications. Thus, WO 2001/000 203 A1 describes guanidinoacetic acid as an energy-supply system and antioxidant for the upper skin layers in which guanidinoacetic acid is mainly applied in the form of creams which protect the skin from unfavourable influences such as solar radiation and stress.

In addition to the advantages of guanidinoacetic acid compared to creatine, the compound, however, has the disadvantage of a very poor solubility in water (1 g in 278 ml water at 15° C.).

From the described disadvantages of the prior art with regard to guanidinoacetic acid, the object was posed for the present invention of improving the solubility of guanidinoacetic acid in water and to further increase the bioavailability while retaining the known good physiological properties of guanidinoacetic acid.

This object is achieved by providing new stable salts and/or addition compounds and/or complex compounds of guanidinoacetic acid with malic acid, aspartic acid, ascorbic acid, succininic acid, pyruvic acid, fumaric acid, gluconic acid, α-ketoglutaric acid, oxalic acid, pyroglutamic acid, 3-nicotinic acid, lactic acid, citric acid, maleic acid, sulfuric acid, acetic acid, formic acid, 2-hydroxybenzoic acid, L-carnitine, acetyl-L-carnitine, taurine, betaine, choline, methionine and lipoic acid as well as in the form of sodium, potassium or calcium guanidino acetate.

It has surprisingly turned out that not only could the object be achieved since the claimed salts and/or addition compounds and/or complex compounds have a considerably higher water solubility compared to guanidinoacetic acid, but also that the new compounds are at least equal to guanidinoacetic acid with regard to their stability and bioavailability.

In addition to the new compounds of guanidinoacetic acid the present invention also concerns a composition that is physiologically effective and which contains at least one of the described salts and/or addition compounds and/or complex compounds of guanidinoacetic acid according to the present invention as an active ingredient.

The present invention also encompasses the use of this composition as an animal feed, as a dietary supplement or in the medical field and especially in the form of powders, granulates, lozenges, capsules, pellets, solutions, juices or jelly products. In this connection it may be advisable depending on the respective concrete application case to use the salts and/or addition compounds and/or complex compounds of guanidinoacetic acid in combination with other physiologically active substances in which case carbohydrates, fats, amino acids, proteins, vitamins, mineral substances, trace elements and derivatives thereof and any mixtures thereof are particularly suitable.

Thus, the present invention also concerns animal feeds, dietary supplements as well as pharmaceutical preparations which contain the salts, addition compounds or complex compounds according to the invention.

A further advantage in this connection has turned out to be the fact that the salts and/or addition compounds and/or complex compounds of guanidinoacetic acid can be used in a relatively broad dosage range in which the single doses as well as the daily doses are not subject to serious limitations. According to the invention the claimed use takes place in single doses of 0.001 to 1 g/kg body weight and/or in daily doses of 0.001 to 50 g.

If the use according to the invention is as a dietary supplement for humans, which takes preferential consideration, uses in the school, sport, convalescence and/or in the geriatric field come in particular into consideration.

The use of the salts and/or addition compounds and/or complex compounds of guanidinoacetic acid as a feed additive is regarded as being preferred especially for animals in competitive sports. In addition the new salts and/or addition compounds and/or complex compounds of guanidinoacetic acid can be used as a feed substitute for wet and dry feeds for dogs and cats in which positive effects on the immune system and the general conditions of the animals deserve special note.

Furthermore, the claimed salts and/or addition compounds and/or complex compounds of guanidinoacetic acid can also be used as a feed additive for breeding animals and fattened animals and in this connection especially for pigs, horses, poultry and fish where their use as a substitute for animal and/or fish meal as well as for products produced therefrom has proven to be particularly advantageous. In this connection the substitution can be a partial or complete substitution.

The salts and/or addition compounds and/or complex compounds of guanidinoacetic acid can also be used within the scope of the present invention in cosmetic or dermatological preparations in accordance with the fields of application that are known for example for creatine. This results in considerable advantages for the formulation due to the high stability and solubility of the claimed compounds, and synergistic effects with regard to efficacy between guanidinoacetic acid and the respective reaction partners are also observed. Preferred preparations are those which are present in the form of creams, lotions, sprays, mousse, aqueous or aqueous-ethanolic solutions, impregnation media for cloths, water-free or water-containing crayons or microemulsions. The topical application fields is regarded as being especially preferred.

Overall the new stable salts and/or addition compounds and/or complex compounds of guanidinoacetic acid of the present invention offer much more than only new alternatives to the known creatine compounds and free guanidinoacetic acid because the properties of the new salts and/or addition compounds and/or complex compounds of guanidinoacetic acid overcome the disadvantages of the known compounds above all in the preferred application fields and are thus very considerable improvements.

The following examples illustrate the breadth of the present invention.

EXAMPLES

1. Dietary Supplement

Typical compositions of tasty formulations are listed in the following whose components have simply been mixed in a dry form at room temperature. It is recommended to dissolve the powder formulations in 200 ml fruit juice and/or water before their oral ingestion.

| | | |
|---|---|---|
| 1.1 | 1500 mg | glucosamine |
| | 750 mg | guanidinoacetic acid α-ketoglutarate |
| | 720 mg | magnesium L-hydrogen aspartate |
| | 2000 mg | glucose |
| | 500 mg | ascorbic acid |
| 1.2 | 400 mg | chondroitin sulfate |
| | 500 mg | guanidinoacetic acid pyruvate |
| | 2000 mg | dicalcium phosphate |
| | 400 mg | $(MgCO_3)_4$•$Mg(OH)_2$•$H_2O$ = about 100 mg |
| | 500 mg | vitamin C |
| 1.3 | 1000 mg | glucosamine |
| | 300 mg | chondroitin sulfate |
| | 2800 mg | guanidinoacetic acid aspartate |
| | 3100 mg | creatinol-O-phosphate |

2. Feed Additive 2.1 A formulation consisting of 5000 mg guanidinoacetic acid malate and 5000 mg inulin was introduced into a typical formulation of feed pellets as a feed supplement for horses.

2.2 A formulation consisting of 7000 mg guanidinoacetic acid lactate, 750 mg carnitine tartrate, 100 mg sucrose stearate, 160 mg talcum and 1090 mg fructose was introduced into the basic bulk for dog biscuits.

2.3 The following formulation was introduced homogenously as a master batch into a commercially canned cat food mixture: 3000 mg guanidinoacetic acid citrate, 3000 mg creatine, 40 mg magnesium stearate, 25 mg carboxymethyl-cellulose and 135 g lactose.

2.4 Feed for fattened chicken

It was found that the addition of 0.2% by weight guanidinoacetic acid lipoate (0.2 g/kg) to the air-dried feed for a 42 day fattening period increased the end weight by 5% compared to previous feeding methods without guanidinoacetic acid. This increase in weight was achieved solely by a meat increase but not by increases in fat or water retention (improvement of the lean body mass index) whereby the meat also had an improved quality. In addition the consumption of feed decreased by about 6% compared to previous feeding methods.

3. Preparations for Cosmetic Creams 1.2% guanidinoacetic acid citrate was homogeneously introduced into a commercial water-in-oil base cream. The cream is suitable for among others treating sensitive, deficient and hypoactive skin conditions. In addition it acts against premature skin ageing and environmentally induced negative changes in the skin.

The invention claimed is:

1. A method comprising increasing creatine in the muscle of a subject by administering to said subject a composition comprising at least one guanidinoacetic acid salt comprising (i) guanidinoacetic acid and (ii) malic acid, ascorbic acid, succinic acid, pyruvic acid, fumaric acid, gluconic acid, α-ketoglutaric acid, oxalic acid, pyroglutamic acid, 3-nicotinic acid, citric acid, maleic acid, sulfuric acid, acetic acid, formic acid, 2-hydroxybenzoic acid, L-carnitine, acetyl-L-carnitine, taurine, betaine, choline or lipoic acid.

2. The method of claim 1, wherein said composition further comprises at least one additional substance selected from the group consisting of carbohydrates, fats, amino acids, proteins, vitamins, mineral substances, trace elements, derivatives thereof and mixtures thereof.

3. The method of claim 1, wherein said composition is in the form of a powder, a granulate, a lozenge, a capsule, a pellet, a solution, a fruit juice or a jelly product.

4. The method of claim 1, wherein a sufficient amount of said composition is administered in an amount sufficient to provide a single dose of 0.001 to 1 g/kg of at least one guanidinoacetic acid salt or addition or complex compound per body weight of said subject.

5. The method of claim 1, wherein a sufficient amount of said composition is administered to the subject to provide a single dose of 0.001 to 50 g of said at least one guanidinoacetic acid salt.

6. The method of claim 1, wherein said subject is a mammal.

7. The method of claim 6, wherein said mammal is a human, dog, cat, pig, or horse.

8. The method of claim 1, wherein the subject is a chicken.

9. The method of claim 1, wherein said subject is a human that attends school, plays sports, is a convalescent, or is a geriatric.

10. A method comprising increasing muscle mass of a subject by administering to said subject a composition comprising at least one guanidinoacetic acid salt comprising (i) guanidinoacetic acid and (ii) malic acid, ascorbic acid, succinic acid, pyruvic acid, fumaric acid, gluconic acid, α-ketoglutaric acid, oxalic acid, pyroglutamic acid, 3-nicotinic acid, citric acid, maleic acid, sulfuric acid, acetic acid, formic acid, 2-hydroxybenzoic acid, L-carnitine, acetyl-L-carnitine, taurine, betaine, choline or lipoic acid.

11. A method comprising increasing the bioavailability of guanidinoacetic acid in a subject by administering to said subject a composition comprising at least one guanidinoacetic acid salt comprising (i) guanidinoacetic acid and (ii) malic acid, ascorbic acid, succinic acid, pyruvic acid, fumaric acid, gluconic acid, α-ketoglutaric acid, oxalic acid, pyroglutamic acid, 3-nicotinic acid, citric acid, maleic acid, sulfuric acid, acetic acid, formic acid, 2-hydroxybenzoic acid, L-carnitine, acetyl-L-carnitine, taurine, betaine, choline or lipoic acid.

12. An animal feed or dietary supplement comprising at least one guanidinoacetic acid salt comprising (i) guanidinoacetic acid and (ii) at least one acid selected from the group consisting aspartic acid, succinic acid, pyruvic acid, fumaric acid, gluconic acid, α-ketoglutaric acid, pyroglutamic acid, citric acid, maleic acid, sulfuric acid, acetic acid, formic acid and lipoic acid.

13. The animal feed or dietary supplement according to claim 12, wherein the at least one acid is selected from the group consisting of succinic acid, pyruvic acid, fumaric acid, gluconic acid, α-ketoglutaric acid, pyroglutamic acid, citric acid, maleic acid, sulfuric acid, acetic acid, formic acid and lipoic acid.

14. A method comprising increasing creatine in the muscle of a subject by administering to said subject a sufficient amount of the animal feed or dietary supplement of claim 12, to increase creatine in said muscle of said subject.

15. A method comprising increasing creatine in the muscle of a subject by administering to said subject a sufficient amount of the animal feed or dietary supplement of claim 13, to increase creatine in said muscle of said subject.

16. A method comprising increasing creatine in the muscle of an animal by administering to said animal a sufficient amount of an animal feed, to increase creatine in said muscle of said animal, wherein said animal feed comprises at least one guanidinoacetic acid salt comprising (i) guanidinoacetic acid and (ii) at least one acid selected from the group consisting of aspartic acid, succinic acid, pyruvic acid, fumaric acid, gluconic acid, α-ketoglutaric acid, pyroglutamic acid, citric acid, maleic acid, sulfuric acid, acetic acid, formic acid and lipoic acid.

17. The method according to claim 16, wherein the at least one acid is selected from the group consisting of succinic acid, pyruvic acid, fumaric acid, gluconic acid, α-ketoglutaric acid, pyroglutamic acid, citric acid, maleic acid, sulfuric acid, acetic acid, formic acid and lipoic acid.

18. The method of claim 14, wherein the animal feed or dietary supplement further comprises at least one additional substance selected from the group consisting of carbohydrates, fats, amino acids, proteins, vitamins, mineral substances, trace elements, derivatives thereof and mixtures thereof.

19. The method of claim 14, wherein said animal feed or dietary supplement is in the form of a powder, a granulate, a lozenge, a capsule, a pellet, a solution, a fruit juice or a jelly product.

20. The method of claim 14, wherein a sufficient amount of said composition is administered in an amount sufficient to provide a single dose of 0.001 to 1 g/kg of said at least one guanidinoacetic acid salt per body weight of said subject.

21. The method of claim 14, wherein a sufficient amount of said composition is administered to the subject to provide a single dose of 0.001 to 50 g of said at least one guanidinoacetic acid salt.

22. The method of claim 16, wherein said subject is a mammal.

23. The method of claim 16, wherein said animal is a dog, cat, pig, or horse.

24. The method of claim 16, wherein said animal is a chicken.

25. The method of claim 14, wherein said subject is a human that attends school, plays sports, is a convalescent, or is a geriatric.

26. The method of claim 15, wherein said subject is a human that attends school, plays sports, is a convalescent, or is a geriatric.

27. The method of claim 15, wherein the animal feed or dietary supplement further comprises at least one additional substance selected from the group consisting of carbohydrates, fats, amino acids, proteins, vitamins, mineral substances, trace elements, derivatives thereof and mixtures thereof.

28. The method of claim 15, wherein said animal feed or dietary supplement is in the form of a powder, a granulate, a lozenge, a capsule, a pellet, a solution, a fruit juice or a jelly product.

29. The method of claim 15, wherein a sufficient amount of said composition is administered in an amount sufficient to provide a single dose of 0.001 to 1 g/kg of at least one guanidinoacetic acid salt per body weight of said subject.

30. The method of claim 15, wherein a sufficient amount of said composition is administered to the subject to provide a single dose of 0.001 to 50 g of said at least one guanidinoacetic acid salt.

* * * * *